(12) United States Patent
Kirschman

(10) Patent No.: US 8,535,356 B2
(45) Date of Patent: Sep. 17, 2013

US008535356B2

(54) SCREW IMPLANT AND SYSTEM AND METHOD FOR LOCKING A SCREW IN AN IMPLANT PLATE

(75) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 438 days.

(21) Appl. No.: 12/612,209

(22) Filed: Nov. 4, 2009

(65) Prior Publication Data

US 2011/0106171 A1 May 5, 2011

(51) Int. Cl.
*A61B 17/80* (2006.01)

(52) U.S. Cl.
USPC ........... 606/291; 606/286; 606/289; 606/305; 606/308

(58) Field of Classification Search
USPC ................ 606/289, 291, 305, 307, 308, 281, 606/104
See application file for complete search history.

(56) References Cited

U.S. PATENT DOCUMENTS

| | | | |
|---|---|---|---|
| 4,488,543 A | 12/1984 | Tornier | |
| 5,192,327 A | 3/1993 | Brantigan | |
| 5,261,911 A | 11/1993 | Carl | |
| 5,549,612 A | 8/1996 | Yapp et al. | |
| 5,713,899 A | 2/1998 | Marnay et al. | |
| 5,776,196 A | 7/1998 | Matsuzaki et al. | |
| 6,136,002 A | 10/2000 | Shih et al. | |
| 6,159,245 A | 12/2000 | Meriwether | |
| 6,224,602 B1 | 5/2001 | Hayes | |
| 6,258,089 B1 | 7/2001 | Delamarter et al. | |
| 6,261,586 B1 | 7/2001 | McKay | |
| 6,264,655 B1 | 7/2001 | Pisharodi | |
| 6,306,136 B1 | 10/2001 | Baccelli | |
| 6,328,738 B1 | 12/2001 | Suddaby | |
| 6,361,537 B1 | 3/2002 | Anderson | |
| 6,592,586 B1 | 7/2003 | Michelson | |
| 2008/0097444 A1 | 4/2008 | Erickson et al. | |
| 2009/0062862 A1* | 3/2009 | Perrow et al. | 606/280 |

FOREIGN PATENT DOCUMENTS

| | | |
|---|---|---|
| DE | 10101267 A1 | 7/2002 |
| EP | 1561429 A1 | 8/2005 |
| FR | 2856272 A1 | 12/2004 |

* cited by examiner

*Primary Examiner* — Andrew Yang
*Assistant Examiner* — Olivia C Chang
(74) *Attorney, Agent, or Firm* — Jacox, Meckstroth & Jenkins

(57) ABSTRACT

A plate system and method comprising a plate and a screw having an integral resilient lock. The screw comprises a head that has a portion that is adapted to be compressible as it is screwed into bone using a tool. After the screw head is received in the plate and the tool is removed therefrom, the screw head decompresses or expands into a locking or receiving area, thereby locking the screw in the plate. The plate is adapted to have at least one or a plurality of detents or lips for cooperating with at least a portion of the screw head to retain the screw in the plate and prevent it from withdrawing therefrom.

49 Claims, 4 Drawing Sheets

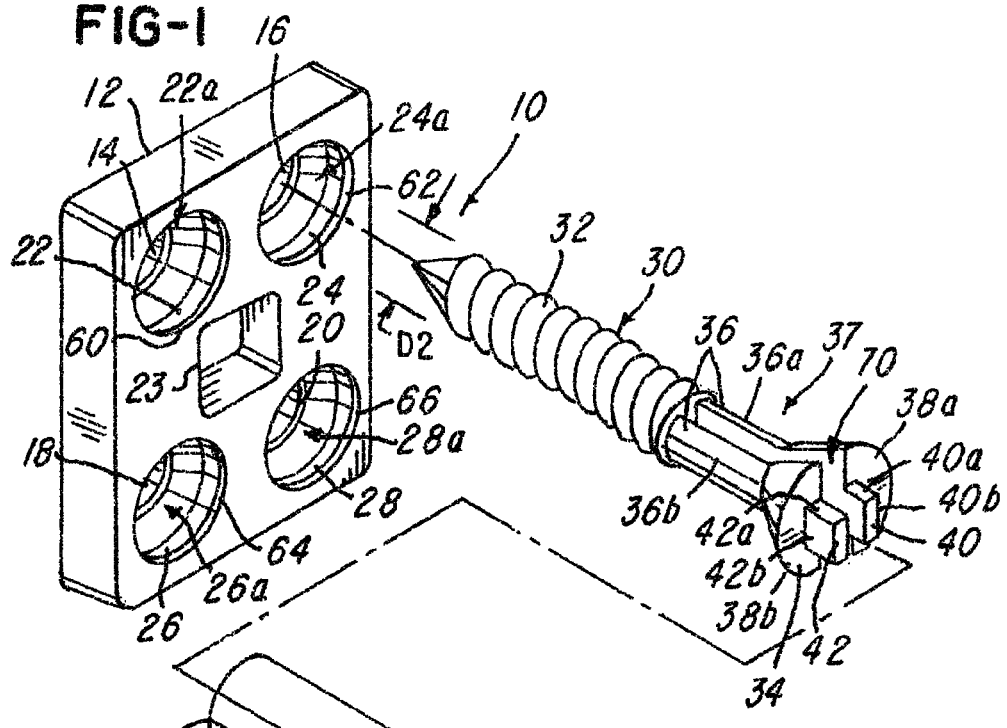
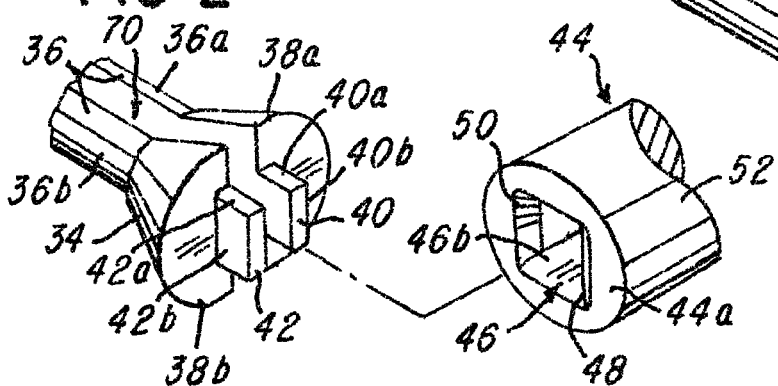

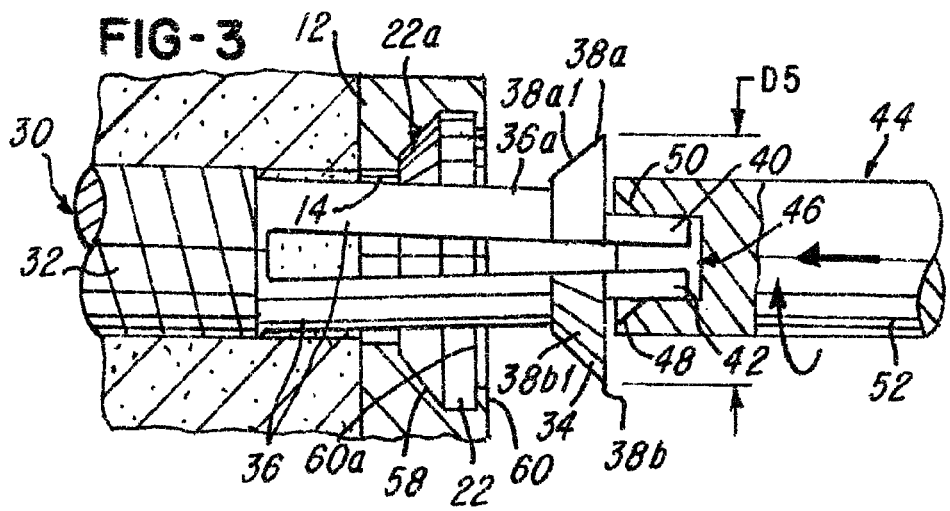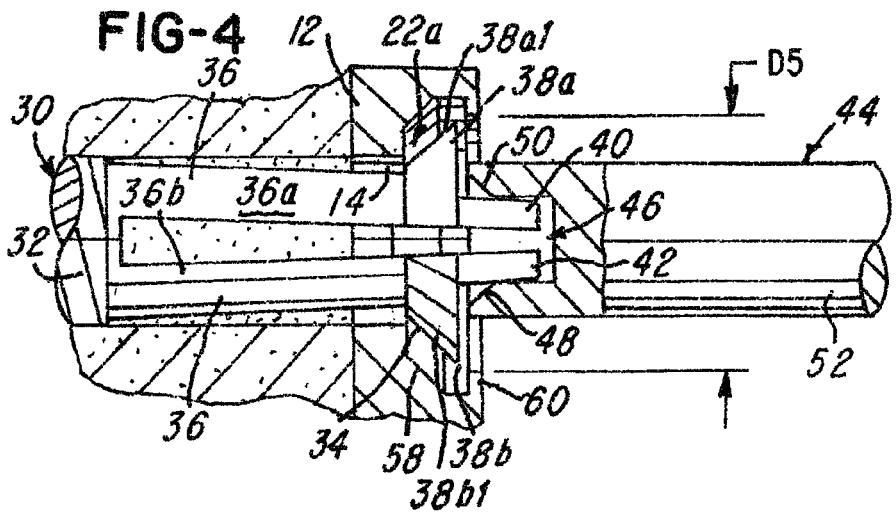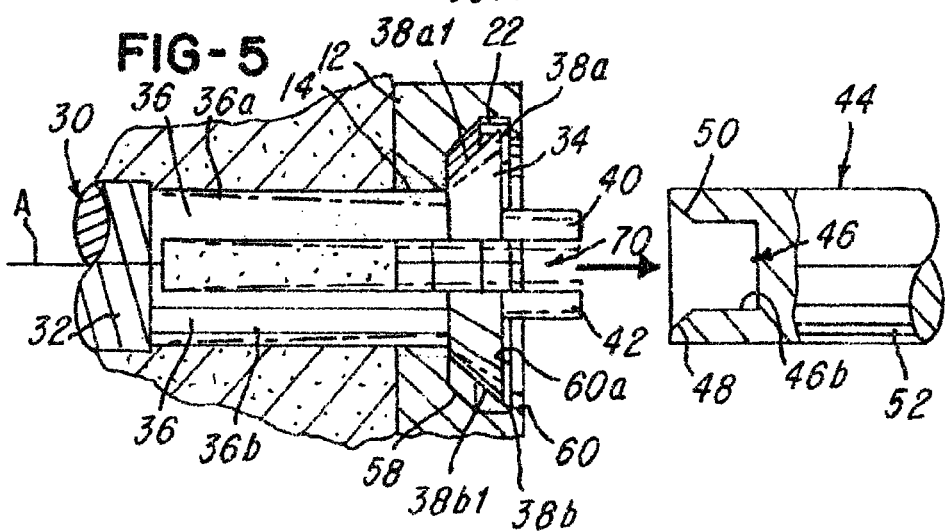

SCREW IMPLANT AND SYSTEM AND METHOD FOR LOCKING A SCREW IN AN IMPLANT PLATE

BACKGROUND OF THE INVENTION

1. Field of the Invention

This invention relates to surgical implants and, more particularly, it relates to a surgical implant plate and a screw having a screw head having at least a portion that is compressible when a tool, such as a screw driver, engages and compresses the portion of the screw head so that it can be received in the plate. Thereafter, the screw head can expand or decompress in order to lock the screw in the plate upon retraction or dismounting of the tool from the screw head.

2. Description of the Related Art

In the past, various types of implant plates and screw locking mechanisms have been proposed. For example, several surgical implant devices and methods are shown in U.S. Pat. Nos. 4,488,543; 5,192,327; 5,261,911; 5,549,612; 5,713,899; 5,776,196; 6,136,002; 6,159,245; 6,224,602; 6,258,089; 6,261,586; 6,264,655; 6,306,136; 6,328,738; 6,361,537; and 6,592,586. Some or all of these devices have improved the success rate and have simplified the surgical techniques in inter-body vertebral fusion.

U.S. Pat. No. 6,258,089 B1 issued Jul. 10, 2001 to Campbell et al. for an Anterior Cervical Plate and Fixation System discloses an anterior cervical plate, along with threaded fasteners for securing the plate to vertebrae or other osseous material. The cervical plate has several pockets or apertures. The pockets have spherical surfaces, and the fasteners have heads with similarly sized spherical surfaces, which when engaged permit each of the fasteners to be oriented at a variety of projection angles with respect to the plate. In connection with each pocket, the cervical plate incorporates a fastener retaining feature. The feature can take the form of a cantilevered tab or a beam supported at its opposite ends, in each case plastically deformable between an open position for admitting the fastener and a closed position for preventing retraction.

U.S. Pat. No. 5,549,612 issued Aug. 27, 1996 to Yapp et al. for Osteosynthesis Plate System discloses an osteosynthesis plate system that is particularly well adapted to securely fuse adjacent cervical vertebrae. The plates are adapted for mounting upon the anterior or posterior surfaces of the vertebrae. Plates for mounting on the anterior vertebral surfaces have a concave bone contacting surface and a bone screw locking mechanism integral with each screw hole. Moreover, the bone contacting surface of the plate has a plurality of bone penetrating protrusions to more securely affix the plate to bone. Plates for mounting on the posterior vertebral surfaces also have bone penetrating protections on their bone contacting surfaces. Such plates are formed so as to have a curved bone contacting surface that is concave in the transverse axis of the plate and convex in the longitudinal axis of the plate. The screw holes of such plates are constructed so as to guide a bone screw along a desired angle to improve the anchoring of the screws in bone.

One drawback of the plates and screw systems of the past is that they were relatively complicated to machine and manufacture and oftentimes required a large thickness in order to provide enough material that will permit the plate to be machined to provide the integral arms and locks.

What is needed, therefore, is a screw, system and method that reduces the number of steps required to attain a screw-plate locked engagement during a surgical procedure.

SUMMARY OF THE INVENTION

It is, therefore, one object of the invention to provide an integral and compressible screw, system and method having a screw locking mechanism that reduces the number of steps required to attain screw-plate engagement and locking during a surgical procedure.

Another object of the invention is to provide a screw locking system and method that will locate the locking mechanism on the screw, rather than the plate.

Still another object of the invention is to provide a system, method and screw-plate locking mechanism that will permit an improved and simpler plate design and that can, for example, reduce a thickness of the plate or provide other machining and manufacturing advantages.

In one aspect, one embodiment comprises a plate system comprising a plurality of screws, each of the plurality of screws having a shank and the screw head, a plate having a plurality of apertures for receiving the plurality of screws, respectively, the plate further comprising a plurality of the detent portions associated with the plurality of apertures, respectively, the plurality of detent portions defining a plurality of screw head receiving areas associated with the plurality of apertures, respectively, for receiving at least a portion of the screw head after the screw is screwed into bone, the at least a portion of the screw head being adapted to be compressible when the screw is screwed into bone and expandable so that it can be received in at least one of the at least one of the plurality of screw head receiving areas, the at least a portion of the screw head cooperating with at least one of the plurality of detent portions to restrict or prevent the screw from withdrawing from the plate.

In another aspect, another embodiment comprises a method for locking a plurality of screws in a plate and preventing them from withdrawing from the plate, each of the plurality of screws comprising a screw head, the method comprising the steps of providing the plate, the plate having a plurality of apertures and a plurality of receiving areas associated with the plurality of apertures, respectively, providing each screw head with a compressible portion, the compressible portion being resilient and compressible when the screw is screwed into bone and expandable so that the compressible portion can expand and be received in at least one of the plurality of receiving areas, the compressible portion of the screw head of each of the plurality of screws cooperating with at least one of the plurality of receiving areas to which it is associated and preventing the screw from withdrawing from the plate.

In still another aspect, another embodiment comprises a bone screw for use in an implant plate comprising a shank and a bone screw head, the bone screw head comprises a compressible portion, the compressible portion being resilient an compressible when the screw is screwed into bone and expandable so that the compressible portion can expand and be received in at least one of a plurality of receiving areas in the implant plate, the compressible portion of the bone screw head of each of the plurality of screws being compressible when the bone screw is screwed into bone and expandable after it is received in the implant plate in order to prevent the screw from withdrawing from the plate.

These and other objects and advantages of the invention will be apparent from the following description, the accompanying drawings and the appended claims.

BRIEF DESCRIPTION OF THE DRAWINGS

FIG. 1 is a perspective, exploded view of a screw, system and method in accordance with one embodiment of the invention;

FIG. 2 is a fragmentary view illustrating a tool in operative relationship with a compressible head on the screw;

FIG. 3 is a fragmentary view illustrating a screw being received in a plate;

FIG. 4 is a fragmentary view illustrating a portion of the screw being compressed after the screw is received in the tool and as the screw is screwed into the bone;

FIG. 5 is a view of the screw after the tool is removed from the screw head, illustrating the screw head expanding to an expanded and locked position where a surface of at least a portion of the screw head becomes generally opposed to at least one detent, such as a lip, associated with a screw receiving aperture in the plate;

DETAILED DESCRIPTION OF THE PREFERRED EMBODIMENTS

Figure 6:
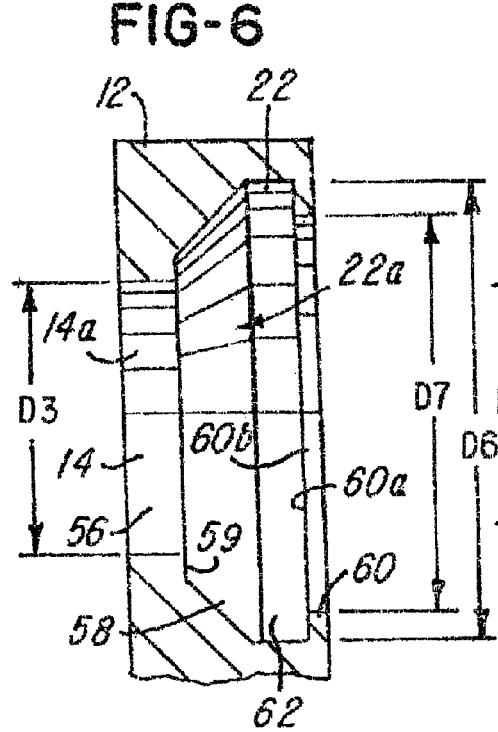
FIG. 6 is a sectional and fragmentary view illustrating details of one of a plurality of receiving areas in the plate.

Referring now to FIGS. 1-14, a system 10 and tool-actuated locking screw mechanism and locking method are shown. The system 10 comprises a plate 12 having a plurality of apertures 14, 16, 18 and 20. The plate 12 may comprise more or fewer apertures if desired and may comprise at least one or a plurality of windows 23 for viewing a graft area (not shown) between two vertebrae to be fused together in a manner conventionally known.

The plurality of apertures 14-20 each comprise an undercut or interior and generally U-shaped wall 22, 24, 26 and 28, respectively, that define a plurality of receiving areas, apertures, undercuts or continuous undercuts 22a, 24a, 26a and 28a whose purpose and function will be described later herein. For ease of illustration, a sectional fragmentary view of the receiving area 22a is shown and described later herein relative to FIG. 6.

The system 10 comprises at least one or a plurality of screws 30 for securing the plate 12 to at least one or a plurality of vertebrae (not shown). For ease of illustration, a single screw 30 is shown and described, and it should be understood that in the example, a single screw 30 is received in each of the plurality of apertures 14-20. As shown in FIG. 1, each screw 30 comprises a threaded portion or shank 32 and a screw head 34. The screw head 34 comprises at least a portion that is adapted to be elastic, resilient or compressible and define a compressible portion 36. In the embodiment being described, the compressible portion 36 comprises a first elongated portion or resilient portion 36a and a generally opposing second elongated portion or resilient portion 36b as shown. Note that the dimension or diameter D1 (FIG. 7) of the elongated portion 36b is slightly smaller than a diameter D2 (FIG. 1) of the threaded portion 32. The benefit of this design is described later herein.

The screw head 34 further comprises a first head portion 38a that is integrally formed with the first elongated portion 36a as shown and a second head portion 38b that is integrally formed with the second elongated portion 36b as shown. The first head portion 38a and second head portions 38b comprise a first male projection 40 and a second male projection 42, respectively, that define or provide a plurality of compressible portions. The first and second male projections 40 and 42 are integrally formed with the head portion 38a and 38b, respectively, as shown and extend generally longitudinally in a direction that is generally parallel to an axis of the head.

The system 10 also comprises a tool 44 having a female working opening 46 (FIG. 2) that is adapted to receive and move or compress the first and second male projections 40 and 42 toward each other and toward an axis of the screw 30 when the tool 44 is mounted thereon. The tool 44 comprises an end 44a having an interior recessed area or wall 46b that defines the female aperture or female working opening or area 46. As mentioned, this female working opening 46 is adapted and sized to receive the male projections 40 and 42 and compress them together. Note that the female working opening 46 is adapted, sized and has a shape that generally complements the shape of the male projections 40 and 42 when they are compressed together.

Note that the tool 44 comprises one or more beveled surfaces or chamfers 48 and 50 in communication with the wall 44b that facilitate guiding ends or surfaces 40a and 42a (FIG. 1) into the female working opening 46 and compressing the male projections 40 and 42, respectively, and guiding them toward each other and toward an axis A (FIG. 5) of the screw 30. The tool 44 comprises a shaft 52 which is coupled to or integrally formed with a handle 54 for gripping and rotating the tool 44 and screwing the screw 30 into bone. The tool shaft 52 may be of any desired length, a tool (not shown) with multiple interchangeable shafts (not shown) may be provided, or multiple tools (not shown) having shafts 52 of different lengths.

Returning to the illustration in FIG. 1, it should be understood that the first and second elongated portions 36a and 36b are compressible, resilient and elastic and moveable in the direction of double arrow X (FIG. 7) and is adapted to permit compression of at least a portion of the screw head 34 when the tool 44 is engaged with or mounted on the screw head 34. As will be described later herein relative to FIGS. 3-14, removal of the tool 44 from the first and second male projections 40 and 42 results in spontaneous expansion of the at least a portion 36 of the screw head 34, as illustrated in FIGS.

4-5. In the illustration being described, the first and second elongated portions 36a and 36b are elastic and/or resilient and adapted to permit the first and second head portions 38a and 38b, respectively, to move toward each other when the tool 44 is mounted thereon and then permit the first and second male projection portions to decompress, expand or move away from each other when the tool 44 is removed from the screw head 34 in the manner described herein.

As mentioned earlier, the plate 12 comprises the plurality of apertures 14-20 having the associated recessed area or internal concavities 22a-28a, respectively, mentioned earlier. For ease of illustration, the wall 22 and associated receiving area 22a will be shown and described relative to FIG. 6, but it should be understood that each of the other recessed areas or receiving areas 24a-28a are similarly constructed. As illustrated in FIG. 6, the plate 12 has a generally cylindrical wall 56 that defines a generally cylindrical portion or exit area 14a of the aperture 14. Note that the generally cylindrical portion 14a has a diameter D3 (FIG. 6) that is slightly larger than the diameter D2 (FIG. 1) of the threaded portion 32 of screw 30, but smaller than the diameter D4 (FIG. 7) of the screw head portions 38a and 38b when they are in either a compressed or non-compressed state.

The plate 12 further comprises a frusto-conical wall 58 that couples the wall or surface 22 to a radial wall, lip or seat 59 (FIG. 6). The walls 58 and 59 cooperate and are adapted and sized to provide or define a seat for receiving the tapered walls or surfaces 38a1 and 38b1 associated with the screw head portions 38a and 38b, respectively.

The plate 12 comprises a plurality of detents or lips 60, 62, 64 and 66 (FIG. 1) that are integral with the walls 22-28, respectively. The plurality of detents or lips 60, 62, 64 and 66 cooperate with the plurality of walls 22-28, respectively, to define the undercuts or define radial annular part of areas 22a-28a. For ease of illustration, the operation and function of the screw head receiving area 22a and screw 30 will now be described relative to FIGS. 3-7.

In general and as illustrated, the tool 44 (FIGS. 2-4) is mounted on the first and second male projections 40 and 42, which compresses them together as shown in FIGS. 3 and 4. The tool 44 is rotated to screw the screw 30 into bone after the screw 30 is received in the aperture 14 of plate 12. The first and second portions 38a and 38b of screw head portion 34 comprises surfaces 38a1 and 38b1, respectively. After these surfaces 38a1 and 38b1 move past or clear (FIGS. 4 and 5) the lip or detent 60, the tool 44 may be removed (FIG. 5) from the screw head 34. When the tool 44 is removed from the first and second male projections 40 and 42, the first and second elongated portions 36a and 36b cause the first and second screw head portions 38a and 38b to de-compress or expand into the receiving aperture or undercut 22a, as illustrated in FIGS. 4-5.

Figure 7:
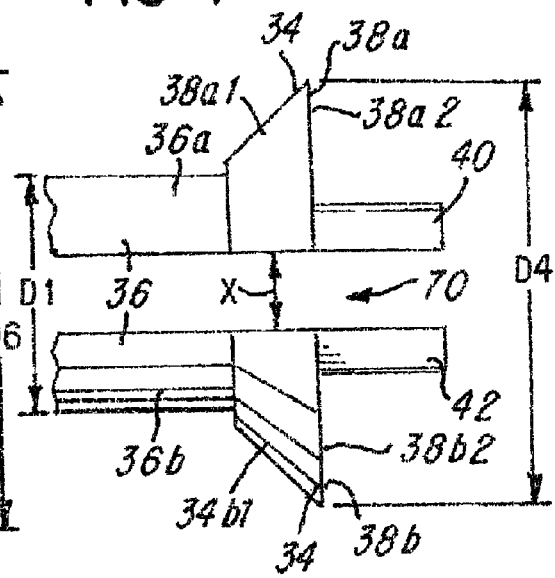
FIG. 7 is a fragmentary view of the screw in a non-compressed state, illustrating various dimensions and configurations of the screw head.

As illustrated in FIGS. 5 and 7, the screw head 34 has an expanded width or screw head diameter dimension D4 (FIG. 7) and a compressed dimension D5 (FIGS. 3 and 4). The wall 22 comprises a wall diameter D6 (FIG. 6) which is larger than the receiving opening dimension or diameter D7 (FIG. 6) defined by an inner surface 60b of the lip or detent 60. In the illustration, dimension D4 (FIG. 7) is larger than dimension D5 (FIG. 4), but smaller than the dimension D6 (FIG. 6), while the compressed dimension D5 is smaller than both the dimension D6 and the dimension D7. This permits the screw head 34 to be received in the aperture 14 and clear the lip 60 when the portions 38a and 38b are compressed, yet be retained by the lip 60 when the portions 38a and 38b are in the non-compressed or expanded state (FIG. 5).

Thus, the tool 44 is mounted on the male projections 40 and 42 of the screw head 34 to compress the screw head 34 by moving the portions 38a and 38b toward each other and toward the axis A (FIG. 5) of the screw 30. The compressed dimension D5, illustrated in FIG. 3, is slightly smaller than the receiving opening dimension D5 so that as the tool 44 is rotated, the screw head 34 clears the lip 60 as the screw 30 becomes screwed into bone. The screw 30 is screwed into bone until the shoulders or surfaces 38a1 and 38b1 clear or move past the surface 60a of the lip 60 as illustrated in FIGS. 3-5. Thereafter, the tool 44 may be removed from the screw head 34 (FIG. 5) which permits the portions 38a and 38b of screw head 34 to resiliently or elastically expand until the surfaces 38a2 and 38b2 (FIG. 7) become generally opposed to the surface 60a of the internal lip or detent 60 as shown in FIG. 5. Notice in FIG. 5 that when this occurs, the surfaces 38a2 and 38b2 cooperate with that surface 60a to retain and lock the screw 30 in the plate 12 and prevent the screw 30 from withdrawing, for example, in an axial direction away from the bone (i.e., to the right as viewed in FIG. 5).

Note in FIG. 5 that the diameter or dimension D1 (FIG. 7) of the screw 30 in the elastic or resilient portions 36a and 36b defines an area or region 37 (FIG. 1) of flexion. This dimension D1 in region 37 is slightly smaller in diameter or cross-section than the diameter or dimension D2 (FIG. 1) of the threaded portion 32. This prevents external bone from engaging and/or compressing the resilient portions 36a and 36b which could interfere with the elastic or resilient re-expansion of the resilient portions 36a and 36b after the tool 44 has been removed from the screw head 34 as illustrated in FIGS. 4 and 5.

At this point, the surfaces 38a2 and 38b2 clear the lip 59 before the screw 34 bottoms out. The surgeon then releases the tool 44 and the screw 34 re-expands. The bottom surface 41 (FIG. 7) of the screw engages the annular seat 59, thereby preventing the screw 34 from travel.

Figure 9:
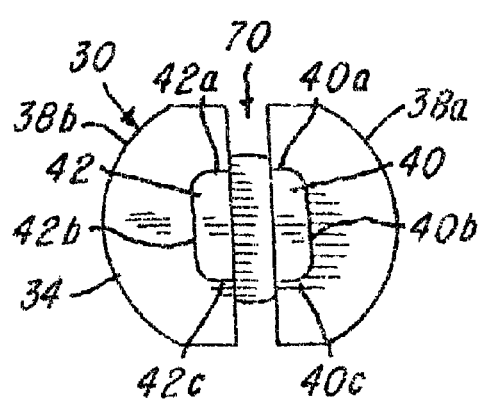
FIG. 9 is a plan view of a screw head in accordance with one embodiment of the invention illustrating an internal concavity or aperture in the screw head which defines a compressible portion on the screw head in the form of a compressible pair of screw head portions each having a male projection.
Figure 10:
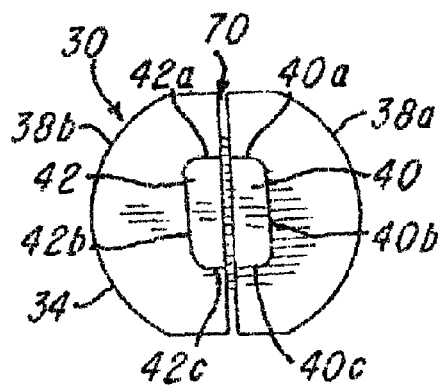
FIG. 10 is a view of the embodiment in FIG. 9 after at least a portion of the screw has been compressed, illustrating the projections cooperating to provide a working surface that can be engaged by a tool and rotatably driven.

In the illustration being described, note that the screw 30 comprises a concavity 70 (FIGS. 1, 2, 9 and 10) that defines the generally opposing first and second elongated portions 36a and 36b and the screw head portions 38a and 38b as shown. As mentioned earlier, the first and second male projection portions 40 and 42 of the screw head 34 are adapted, sized and shaped to provide a rotatably drivable working surface when they are compressed by the working end 44a of the tool 44. In this regard, when the male projections 40 and 42 are compressed toward each other, as illustrated in FIG. 10, they define a generally polygonal shape, such as a rectangular or square shape. The male projections 40 and 42 may also be adapted, sized and shaped to any desired configuration that will enable the at least a portion 36 of the screw head 34, such as the male projections 40 and 42, to be compressed toward the axis of screw 30 or toward each other so that they can be received in the working area 46 of tool 44 and rotatably driven. Similarly, the interior wall 44b that defines the female aperture or female working opening 46 is adapted, sized and shaped so that it complements the shape of the compressed male projections 40 and 42, so that the male projections 40 and 42 can be rotatably driven by the tool 44 in order to screw the screw 30 into bone, although not shown, The concavity 70 or separating area may comprise one or more separating areas to define the pair of elongated members 36a and 38a. FIGS. 9 and 10 illustrate the screw 30 having the screw head 34 and concavity 70 that provides or defines the pair of generally opposing male projections 40 and 42 as shown. Again, note that when the screw head portions 38a and 38b are compressed together, the male projections 40 and 42 have surfaces 40a, 40b, 40c and 42a, 42b and 42c (FIGS. 9 and 10) that cooperate to define the generally rectangular (as viewed in FIG. 10) projection that is received in the working end 44a of the tool 44.

Figure 13:
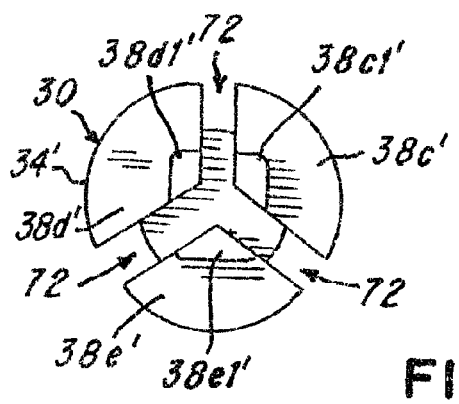
FIG. 13 is a view similar to FIGS. 9 and 11 showing still another embodiment of a screw head in a non-compressed state, with the internal concavity in the screw head defining three screw head portions with each having male projections.
Figure 14:
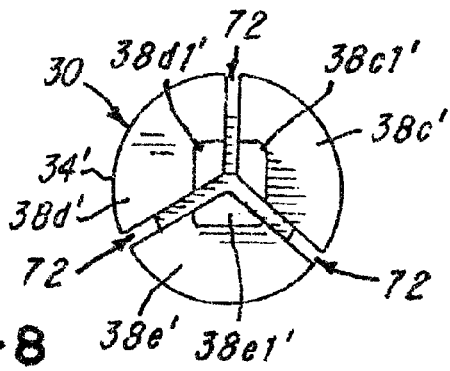
FIG. 14 is a another plan view of the screw head shown in FIG. 13 after it has been compressed to a compressed state and showing the male projections cooperating to define a working surface or projection that can be received in and driven by the tool.
Figure 8:
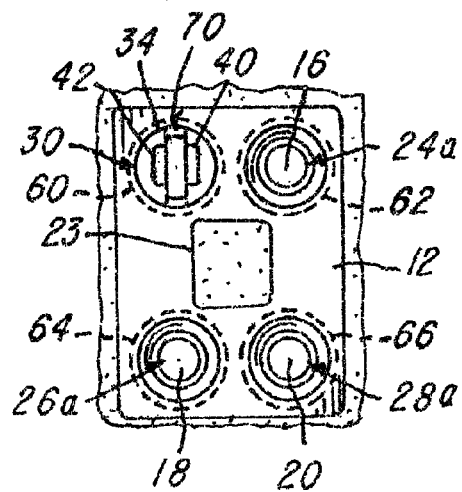
FIG. 8 is a view of the plate illustrating one of the screws locked in the plate after it is driven into bone.

FIGS. 13 and 14 illustrate another embodiment showing a screw 30 having a screw head 34' concavity 72 defining three posts, portions or male projections 30c', 30d' and 30e' shown in an expanded state in FIG. 13. Note that when the screw head portions 38c', 38d' and 38e' are compressed toward each other and toward an axis of the screw 30, the associated surfaces of male projections 38c1', 38d1' and 38e1', respectively, and associated surfaces cooperate to define a generally rectangular or polygonal shape. They are adapted to be received by the working end 44a of the tool 44 which has the female aperture or female working opening 46, which is adapted and sized to complement the shape of the male projections when they are compressed so that the tool 44 can rotatably drive and screw the screw 30' into bone.

Figure 11:
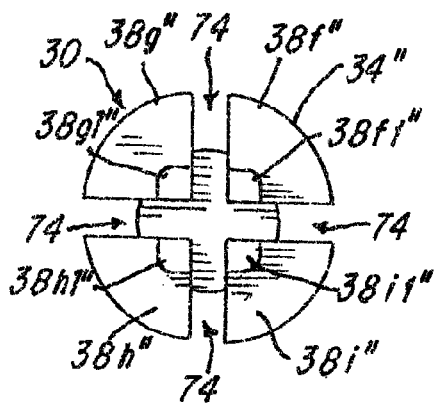
FIG. 11 is a view of another embodiment illustrating the internal concavity in the screw head defining four head portions each having a male projection in a non-compressed state.
Figure 12:
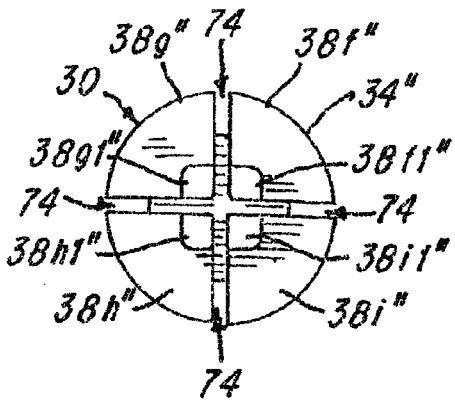
FIG. 12 is a view of the alternate embodiment shown in FIG. 11 after the screw head has been compressed, showing the male projections cooperating to define a drivable working surface that can be received in the tool and rotatably driven.

FIGS. 11 and 12 illustrate yet another illustrative embodiment showing a screw head 34" concavity 74 that defines four generally elongated portions 38f", 38g", 38h" and 38i". In this embodiment, each of the four elongated portions 38f'-38i' comprises the male projections portions 38f1", 38g1", 38h1" and 38i1" as shown in FIG. 11. FIG. 11 illustrates the screw head portions 38f"-38i" in their non-compressed or expanded state when they are not engaged by the tool 44. In contrast, FIG. 12 illustrates the compressed state of the screw head portions 38f"-38i" after the tool 44 is placed on the male projection portions 38f1"-38i1" in the manner described earlier herein. Again, it is important to note that the side wall or surfaces of the male projection portions 38f1"-38i1" cooperate to define a working surface, such as a polygonal, hexagonal, rectangular or square surface that cooperates with and is adapted to be received in the female aperture or female working opening 46 of the tool 44 which has a complementary shape so that the tool 44 can rotatably drive and screw the screw 30 into bone.

While the embodiments shown and described relative to FIGS. 1-14 illustrate two portions 38a and 38b (FIGS. 9 and 10), three portions 30c', 30d' and 30e' (FIGS. 13 and 14) and four portions 38f", 38g", 38h" and 38i" (FIGS. 11 and 12), it should be understood that the screw head 34 could be provided with a concavity that defines more projection portions if desired.

Returning now to FIG. 6, note that the undercut or receiving area 62 provides a continuous undercut or receiving area 22a about the aperture 14. It should be understood that while the lip 60 in the embodiment being described defines a continuous annular surface 60a surrounding the aperture 14. This lip 60 could also be discontinuous to provide at least one or a plurality of detents that cooperate with one or more of the surfaces 38a2 and 38b2 (FIG. 7) to lock the screw 30 in the plate 12.

Advantageously, a benefit to the embodiments being described herein is a reduction in the number of steps required to remove the screw from the plate screw-plate engagement during a surgical procedure. In this regard, the disengagement of the locking of the screw 30 in the plate 12 occurs when the tool 44 is mounted on the screw head 34. Many prior art systems, for example, require multiple tools, for example, one tool to release the screw lock and another tool to screw the screw.

Moreover, many prior art mechanisms comprised a locking mechanism embodied in the plate or on the plate, whereas the locking mechanism in the illustration being described is embodied and integral with screw 30 rather than the plate. Advantageously, this allows for simpler plate designs. This also permits the plates being made thinner, which is a goal of surgical plate development.

While the system, apparatus and method herein described, and the form of apparatus for carrying this method into effect, constitute preferred embodiments of this invention, it is to be understood that the invention is not limited to this precise method and form of apparatus, and that changes may be made in either without departing from the scope of the invention, which is defined in the appended claims.

What is claimed is:

1. A plate system comprising:
a plurality of screws, each of said plurality of screws having a shank and a screw head;
a plate having a plurality of apertures defined by a plurality of internal walls, respectively, said plurality of apertures being adapted to receive said plurality of screws, respectively, said plate further comprising a plurality of screw head receiving areas associated with said plurality of apertures, respectively, for receiving at least a portion of said screw head after said screw is screwed into bone, said plate further comprising a plurality of detent surfaces associated with and extending into said plurality of screw head receiving areas, respectively;
said at least a portion of said screw head comprising a plurality of compressible portions that are compressible when said screw is screwed into bone and expandable after it is received in at least one of said plurality of screw head receiving areas;
said at least a portion of said screw head having or defining at least one screw surface that cooperates with at least one of said plurality of detent surfaces after said at least a portion of said screw head has been received in said plurality of screw head receiving areas to facilitate preventing said screw from withdrawing from said plate;
a tool having a working end having an interior wall defining a working opening with said interior wall having a fixed shape without moveable parts and being adapted to compress said plurality of compressible portions to a compressed position when said plurality of compressible portions are received in said working opening;
wherein said plurality of compressible portions cooperate, after being received in said working opening and compressed to said compressed position by said internal wall, to define a driving surface that can be rotatably driven by said internal wall in response to rotation of said tool in order to screw said screw into bone;
said plurality of compressible portions being compressed by said internal wall when said screw is screwed into bone and thereafter expandable after said screw is screwed into bone and said tool removed from said screw head so that said at least one screw surface can cooperate with said at least one of said plurality of detent surfaces to retain said screw in said plate;
said fixed shape generally complementing a shape of said driving surface.

2. The plate system as recited in claim 1 wherein said plurality of compressible portions being resilient and applying force against said interior wall of said tool to retain said screw in said tool.

3. The plate system as recited in claim 2 wherein said working end of said tool comprises a female working opening having a first shape, said at least a portion of said screw head comprising a plurality of male projection members that cooperate to define a male projection working surface when said at least a portion of said screw head is compressed after it is received in said female working opening of said tool, said male projection working surface defining a projection shape that generally complements said first shape.

4. The plate system as recited in claim 3 wherein said projection shape comprises a plurality of sides.

5. The plate system as recited in claim 3 wherein said at least a portion of said screw head comprises a projection shape that is generally rectangular.

6. The plate system as recited in claim 5 wherein said projection shape is generally square or rectangular.

7. The plate system as recited in claim 1 wherein said screw head comprises a concavity that defines a plurality of projections that cooperate to define said at least a portion of said screw head.

8. The plate system as recited in claim 7 wherein said plurality of projections extend longitudinally and move substantially simultaneously toward an axis of said screw and cooperate to define a male projection when said screw is screwed into bone.

9. The plate system as recited in claim 8 wherein said system further comprises a tool having a working end, said working end of said tool comprising a female working opening having a first shape, said plurality of projections cooperating to define a male projection working surface after they are received in said female working opening of said tool, said male projection working surface having a projection shape that generally complements said first shape so that said male projection becomes sized and adapted to be received in said female working opening so that said tool can screw said screw into bone.

10. The plate system as recited in claim 1 wherein said plurality of detent surfaces define a plurality of walls, respectively, associated with said plurality of apertures.

11. The plate system as recited in claim 1 wherein each of said plurality of detent surfaces defines a lip associated with each of said plurality of apertures.

12. The plate system as recited in claim 11 wherein said plate has an internal recessed or undercut wall associated with each of said plurality of apertures that cooperate with said lip to define said at least one of said plurality of screw head receiving areas.

13. The plate system as recited in claim 1 wherein said each of said at least a portion of each of said screw head comprising a plurality of elongated members, each of said plurality of elongated members being resilient or elastic so that they can be moved toward each other and define a male projection working surface adapted to be received in a complementary-shaped working area of a tool.

14. The plate system as recited in claim 13 wherein each of said plurality of elongated members extend generally parallel to a longitudinal axis of said screw and have a lateral projection that cooperates with said at least one of said plurality of detent surfaces to retain the screw in the plate after said screw is received in bone and said tool has been removed from said working area of said tool.

15. The plate system as recited in claim 14 wherein said lateral projection defines at least a portion of said screw head.

16. The plate system as recited in claim 10 wherein said plate comprises a plurality of walls associated with said plurality of apertures, respectively, each of said plurality of walls being adapted to define said plurality of screw head receiving areas, respectively, for receiving said at least a portion of said screw head for restricting or preventing said screw from moving in an axial direction.

17. The plate system as recited in claim 16 wherein each of said plurality of walls are generally U-shaped and extend into said plurality of apertures, respectively.

18. The plate system as recited in claim 1 wherein said screw head comprises at least one concavity that defines a plurality of sections that are compressible or moveable toward an axis of said screw to a compressed position.

19. The plate system as recited in claim 18 wherein said plurality of sections cooperate when compressed to a compressed position to define a male member adapted to be received in a tool.

20. The plate system as recited in claim 19 wherein said system further comprises said tool, said tool comprising a working opening for receiving said plurality of sections and for maintaining said plurality of sections in said compressed position.

21. The plate system as recited in claim 20 wherein said tool comprises an end having a recessed wall that defines said working opening, said recessed wall comprising at least one beveled surface for urging said plurality of sections toward said axis of said screw when said tool is mounted on said male member.

22. The plate system as recited in claim 18 wherein said plurality of sections comprises two, three or four sections.

23. A bone screw system for use in an implant plate comprising:
a shank and a screw head;
said screw head comprising a compressible portion, said compressible portion being resilient and compressible when said bone screw is screwed into bone and expandable so that said compressible portion can expand and be received in at least one of a plurality of receiving areas in said implant plate;
said compressible portion of said screw head being compressible when said bone screw is screwed into bone and expandable after it is received in said implant plate in order to prevent said screw from withdrawing from said implant plate;
at least a portion of said screw head comprising a plurality of compressible portions that, when compressed, define a driving surface that is engaged and driven by a working end of a tool, said plurality of compressible portions applying a force against an interior wall of said tool to retain said screw to said working end and to retain said screw in said implant plate after said bone screw is screwed into bone and said tool has been removed from said screw head;
said working end of said tool having an interior wall defining a working opening with said interior wall having a fixed shape without moveable parts and being adapted to compress said plurality of compressible portions to a compressed position when said plurality of compressible portions are received in said working opening;
wherein said plurality of compressible portions cooperate, after being received in said working opening and compressed to said compressed position by said interior wall, to define said driving surface;
said plurality of compressible portions being compressed by said interior wall when said screw is screwed into bone and thereafter expandable after said screw is screwed into bone and said tool removed from said screw head;
said fixed shape generally complementing a shape of said driving surface.

24. The bone screw as recited in claim 23 wherein said screw head further comprises a plurality of sections that are compressible or moveable toward an axis of said bone screw to a compressed position.

25. The bone screw as recited in claim 24 wherein said plurality of sections cooperate when compressed to said compressed position to define a male projection working surface adapted to be received in a tool.

26. The bone screw as recited in claim 25 wherein said male projection working surface comprises a projection shape comprising a plurality of sides.

27. The bone screw as recited in claim 25 wherein said male projection working surface comprises a projection shape that is adapted to be received in and driven by a tool.

28. The bone screw as recited in claim 26 wherein said projection shape is polygonal.

29. The bone screw as recited in claim 27 wherein said plurality of sections comprises two, three or four sections.

30. The bone screw as recited in claim 24 wherein said plurality of sections are defined by a concavity in said screw head.

31. The bone screw as recited in claim 30 wherein said concavity defines two, three or four compressible sections.

32. An implant system comprising:
a plate member having a plurality of screw-receiving openings, each of said plurality of screw-receiving openings having a screw head capturing area and at least one plate member detent associated therewith;
a plurality of screws each having a screw head comprising a plurality of integral compressible detents for receipt in said screw head capturing area;
said plurality of integral compressible detents of each screw being compressible when the screw is screwed into bone and thereafter expanding after said screw is mounted into bone and cooperating with said at least one plate member detent of said plurality of screw-receiving openings to which it is associated to prevent said screw from withdrawing from said plate member; and
a tool having a working end having an interior wall defining a working opening, said interior wall having a fixed shape without moveable parts and being adapted to compress said plurality of integral compressible detents when said plurality of integral compressible detents are received in said working opening;
wherein said plurality of integral compressible detents cooperating, when compressed to a compressed position, to define a driving surface for rotatably driving and screwing said screw into bone in response to a rotation of said tool;
said plurality of integral compressible detents being expandable after said screw is screwed into bone and cooperating with said at least one plate member detent to prevent said screw from withdrawing from said plate member;
said fixed shape generally complementing a shape of said driving surface.

33. The implant system as recited in claim 32 wherein said system further comprises a tool having a working end for compressing said plurality of integral compressible detents after said screw head is received in said working end.

34. The implant system as recited in claim 33 wherein said working end of said tool comprises a female working opening having a first shape, said plurality of integral compressible detents cooperating to define a male projection working surface after they are received in said female working opening of said tool and compressed, said male projection working surface having a projection shape that generally complements said first shape.

35. The implant system as recited in claim 34 wherein said projection shape comprises a plurality of sides.

36. The implant system as recited in claim 35 wherein said projection shape is rectangular.

37. The implant system as recited in claim 35 wherein said projection shape is generally square.

38. The implant system as recited in claim 32 wherein said screw head comprises a concavity that defines said plurality of integral compressible detents.

39. The implant system as recited in claim 38 wherein said plurality of integral compressible detents extend longitudinally and move substantially simultaneously move toward an axis of said screw and cooperate to define a male projection when said screw is screwed into bone.

40. The implant system as recited in claim 39 wherein said system further comprises a tool having a working end, said working end of said tool comprising a female working opening having a first shape, said plurality of integral compressible detents cooperating to define a male projection working surface after they are received in said female working opening of said tool, said male projection working surface having a projection shape that generally complements said first shape so that said male projection becomes sized and adapted to be received in said female working opening so that said tool can screw said screw into bone.

41. The implant system as recited in claim 32 wherein said plate member comprises a plurality of undercuts associated with said plurality of screw-receiving openings, respectively.

42. The implant system as recited in claim 32 wherein said plate member comprises a wall extending into each of said plurality of screw-receiving openings, said wall defining an undercut.

43. The implant system as recited in claim 32 wherein each screw head comprises a concavity that defines a plurality of elongated members, each of said plurality of elongated members being resilient or elastic so that they can be moved toward each other and define a male projection or working surface adapted to be received in a complementary-shaped working area of a tool.

44. The system as recited in claim 43 wherein each of said plurality of elongated members extend generally parallel to a longitudinal axis of said screw and have a lateral projection that cooperates with said at least one of said plurality of integral compressible detents to retain the screw in said plate member after said screw is received in bone and said tool has been removed from said working area of said tool.

45. The implant system as recited in claim 41 wherein said plate member comprises a plurality of walls associated with said plurality of screw-receiving openings, respectively, each of said plurality of walls being adapted to define said plurality of screw-receiving openings, respectively, for receiving said at least a portion of said screw head for restricting or preventing said screw from moving in an axial direction.

46. The implant system as recited in claim 45 wherein each of said plurality of walls defines said at least one plate member detent that cooperates with said plurality of compressible detents to retain said screw head in said plate member.

47. The implant system as recited in claim 43 wherein said system further comprises said tool, said tool comprising a working opening for receiving said plurality of elongated members and for maintaining said plurality of elongated members in a compressed position.

48. The implant system as recited in claim 47 wherein said interior wall comprises a recessed wall that defines said working opening, said recessed wall comprising at least one beveled surface for urging said plurality of elongated members toward an axis of said screw when said tool is mounted on a male working surface.

49. The implant system as recited in claim 43 wherein said plurality of elongated members define two, three or four elongated projections that extend parallel to an axis of said screw.

* * * * *